United States Patent
Becher

(10) Patent No.: US 7,763,274 B2
(45) Date of Patent: Jul. 27, 2010

(54) ADMINISTRATION FORM WITH ACTIVE SUBSTANCE-CONTAINING PARTICLES, FOR APPLICATION ON THE SKIN OR MUCOSA

(75) Inventor: Frank Becher, Koblenz (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 1436 days.

(21) Appl. No.: 10/484,895

(22) PCT Filed: Jul. 11, 2002

(86) PCT No.: PCT/EP02/07716

§ 371 (c)(1),
(2), (4) Date: Mar. 19, 2004

(87) PCT Pub. No.: WO03/011247

PCT Pub. Date: Feb. 13, 2003

(65) Prior Publication Data

US 2004/0191281 A1  Sep. 30, 2004

(30) Foreign Application Priority Data

Jul. 27, 2001 (DE) .................. 101 36 784

(51) Int. Cl.
*A61F 13/00* (2006.01)
(52) U.S. Cl. ....................... 424/449; 424/448
(58) Field of Classification Search ............... None
See application file for complete search history.

(56) References Cited

U.S. PATENT DOCUMENTS

| 5,032,403 A | * | 7/1991 | Sinnreich ................ 424/448 |
| 5,071,645 A | | 12/1991 | Reinhardt et al. |
| 5,147,339 A | * | 9/1992 | Sundstrom ............... 604/307 |
| 5,230,898 A | | 7/1993 | Horstmann et al. |
| 5,232,702 A | * | 8/1993 | Pfister et al. ............ 424/448 |
| 5,456,917 A | | 10/1995 | Wise et al. |
| 5,629,014 A | * | 5/1997 | Kwiatek et al. .......... 424/449 |
| 6,652,876 B2 | * | 11/2003 | Radloff et al. ........... 424/448 |
| 2003/0232905 A1 | * | 12/2003 | Ives et al. ............... 524/35 |

FOREIGN PATENT DOCUMENTS

| WO | WO 94/07468 A | 4/1994 |
| WO | WO 95/33452 A1 | 12/1995 |
| WO | WO 99/17868 A1 | 4/1999 |

OTHER PUBLICATIONS

Yu et al, "A staining technique for evaluating the pore structure variations of microcrystalline cellulose powders" Powder Technology, 98, (1998) p. 135-138.*

* cited by examiner

*Primary Examiner*—Robert A Wax
*Assistant Examiner*—Bethany Barham
(74) *Attorney, Agent, or Firm*—Birch, Stewart, Kolasch & Birch, LLP

(57) ABSTRACT

Administration forms for application to the skin or mucosa, comprising a carrier matrix and at least one active substance, are characterized in that the carrier matrix has a plurality of particles having open pores or containing capillary spaces, said particles serving as active substance reservoir and containing at least one active substance.

39 Claims, No Drawings

ADMINISTRATION FORM WITH ACTIVE SUBSTANCE-CONTAINING PARTICLES, FOR APPLICATION ON THE SKIN OR MUCOSA

This is a National Stage application of International Application No. PCT/EP02/07716 filed Jul. 11, 2002. This Nonprovisional application claims priority under 35 U.S.C. §119 (a) on Patent Application No(s). 101 36 784.8 filed in Germany on Jul. 27, 2001, the entire contents of which are hereby incorporated by reference.

The invention relates to administration forms for application to the skin or mucosa, comprising a carrier matrix and at least one active substance present in particles. The invention more particularly relates to administration forms for transdermal, transmucosal or epicutaneous (topic) application of active substances, such as transdermal therapeutic systems (TTS), topic active substance plasters or transmucosal therapeutic systems.

The manufacture of administration forms of the aforementioned type is frequently performed in such a manner that the active substance, mixed with suitable carrier substances and auxiliary substances, is incorporated in liquid form in the basic or matrix material of the form of medicament and that then the desired form of administration is produced in further process steps.

This approach is, however, disadvantageous for various reasons, in particular in the manufacture of certain types of administration forms.

TTS, active substance plasters or transmucosal therapeutic systems, for example, generally are flat forms of administration of small thickness which, in addition, must have certain physical properties such as strength, elasticity, tackiness or mucoadhesive properties.

If, in the manufacture of such forms of medicaments a liquid active substance or an active substance solution is incorporated into the carrier matrix, this may have as a consequence that in the case of an excessive active substance load the mechanic properties of the carrier material, especially coherence and flexibility, as well as the pressure-sensitive adhesive properties, will be adversely affected.

Owing to the small thickness of these systems it is therefore generally only possible to incorporate relatively small amounts of liquid active substance.

In addition, it has to be taken into consideration that, at the temperatures suitable for the preparation of medicaments, certain active substances are present exclusively as liquids, which means that they can only be processed in liquid form.

The task underlying the invention was therefore to indicate forms of administration or medicinal preparations of the kind mentioned at the beginning, the manufacture of which can start from liquid preparations of active substance, but without the appearance of the above-mentioned disadvantages.

This task is solved by medicinal preparations according to claim 1 and the processes of manufacture according to claims 19 to 23, as well as by the especially preferred embodiments described in the dependent claims.

The invention provides for the carrier matrix of an administration form mentioned in the introductory part of claim 1 to have a plurality of particles containing open-pores or capillary spaces, said particles serving as active substance reservoir.

A particular advantage of this type of administration forms is that the active substance concerned does not have to be distributed uniformly in the carrier matrix or applied thereto in dissolved form, but is instead present in many small reservoir particles. In this way it is possible to considerably reduce the overall amount of this active substance since it is not necessary to homogeneously distribute the active substance. It is sufficient for the active substance to be present in many small particles, and only in these, in a sufficient concentration for it to become effective.

A further advantage consists in the fact that the strength of the administration form, respectively of the carrier matrix, is not adversely affected by the active substance present in particle form since the liquid active substance portions are bound in the particles.

1. The particles according to the invention may be particles which have open pores or contain capillary spaces and which have a large interior surface.
2. They may also be such active substance-containing particles as are obtained by the process described in WO 99/17868.

The following initially relates to the first-mentioned form of particles.

These particles serve as active substance reservoir and contain at least one active substance, preferably in liquid form. "Liquid form" is understood to mean that the active substance itself is present in liquid state, or that it is present as a solution, dispersion, suspension, emulsion or as a liquid active substance preparation.

A main advantage of these active substance preparations consists in that the active substance-containing particles are first loaded with liquid active substance or a liquid active substance preparation, in a manner known to those skilled in the art.

This can be done, in particular in an especially preferred embodiment, by placing the particles containing pores or capillary spaces in a vacuum (preferably in the range of approx. 100 to $10^{-3}$ mbar, more preferably 10 to 0.01 mbar, and most preferably 1 to 0.1 mbar). This has the special advantage of air, which is present in the capillaries in most cases, being removed; as a consequence, the specific weight of the particles is higher and the particles do no longer float on the surface of the active substance liquid. Still in the vacuum, the particles are virtually washed round with the active substance liquid, which can be achieved, for example, by stirring with high-speed stirring apparatuses, shaking, or in any other suitable way. When normal pressure conditions are subsequently established, the active substance liquid is pressed into the capillaries or pores by the air pressure.

In a further preferred embodiment, the particles are incorporated in the active substance liquid, the latter is then subjected to increased pressure (preferably in the range of from 2 to 300 bar, more preferably 10 to 200 bar, most preferably 10 to 100 bar), so that the active substance liquid is pressed into the air-filled pores. Upon subsequent relief of pressure, the air located in the pores will emerge because the adhesion forces of the liquid are greater.

For impregnation, the processes known to those skilled in the art may be utilized (e.g. pressure chamber impregnation of wood).

In a further preferred embodiment, the particles are heated to high temperatures (preferably in the range of from 40 to 200° C., with particular preference 50 to 150° C.), so that the pressure of the air which is present in the pores is low; these hot particles are then washed round with cold active substance fluid, so that it is able to enter into the cavities. "Cold" means that the temperature is lower than that of the particles.

Furthermore, the loading of the particles can be performed in such a manner that the particles are suspended in and mixed with the liquid active substance, respectively the liquid active substance preparation, under normal pressure and at room temperature (approx. 20-30° C.), preferably under stirring.

The above-indicated processes can be combined in a manner known to those skilled in the art, for example by alternate pressure impregnation and vacuum impregnation. The loaded particles are, if necessary, separated from the excess active substance fluid, for instance by sedimentation or filtration.

Subsequently, the particles, which are loaded with liquid active substance, can be incorporated in solid form, e.g. as a powder, in the carrier matrix of the respective active substance preparation. In this process, apart from the active substance liquid enclosed in the particles no liquid, or only a negligible amount, is introduced into the carrier matrix mass, so that the structure, consistency, tackiness, elasticity and other properties of the matrix material are not adversely affected. In any case, it is possible in this way to incorporate larger quantities of an active substance present in liquid form into a medicinal preparation than would be the case when employing conventional modes of manufacture. For this reason, in the manufacture of the inventive forms of medicaments it is possible to employ substantially the same methods and apparatuses as are used for the processing of solid medicinal active agents. In particular, the invention enables the production of flat, thin forms of administration such as transdermal therapeutic systems or mucoadhesive medicament forms, starting from liquid active substance preparations.

It is of particular advantage that the various particles can also be loaded with different active substances so that it is readily possible to prepare combined preparations such as, for example, gestagen-estrogen plasters.

It is also particularly advantageous that, in addition, other particles can also be loaded with liquid plasticizers and/or (skin-penetration) enhancers. Alternatively, these substances may also be contained along with the active substance in the same particles.

Plasticizers, respectively enhancers can be selected from the following substances and substance groups: Saturated or unsaturated fatty acids, hydrocarbons, straight-chain or branched fatty alcohols, dimethyl sulfoxide, propylene glycol, decanol, dodecanol, 2-octyl dodecanol, glycerol, isopropylidene glycerol, transcutol (=diethylene glycol monoethyl ether), DEET (=N,N-diethyl-m-tolueneamide), solketal, ethanol, 1,2-propanediol, or other alcohols, menthol and other ethereal oils or components of ethereal oils, lauric acid diethanolamide, D-alphatocopherol and dexpanthenol; the above list is not complete.

Advantageously, various particle types and sizes can be utilized in order to achieve differentiated release behaviour.

A further advantage consists in the fact that by using liquid-filled active substance particles, it is possible to improve safety in the production of medicines. This is particularly true if there is a risk of the personnel becoming contaminated with active substances, especially with toxic substances.

As porous particles that can be loaded with liquid active substances or active substance solutions, those substances are particularly suitable which are selected from the group comprising activated charcoal particles, particles of porous minerals, especially kieselguhr particles, diatomaceous earth, pumice, lava, bentonite, ceramic or clay particles, silica gel particles, silicon monoxide particles, zeolite, as well as particles of natural or synthetic sponges or of solidified foams. "Porous particles" is understood to also include those particles which have a capillary structure.

A common property of the particles mentioned is that because of their pores or capillaries they have a large internal surface, which is a basic prerequisite for a high active substance load.

Suitable as synthetic sponges or foams are, depending on the intended use, both biodegradable materials (e.g. solidified gelatine foams or collagen foams) and nondegradable materials (e.g. polyurethane foams, microcellular polyester foams or polyether foams).

Also considered are superabsorbers such as polymers which are capable of swelling, as described, for example, in PCT/EP 95/02120.

When selecting the particles, care must be taken that the selected type is suitable and harmless, from a pharmacological and toxicological point of view, for the intended mode of application (e.g. oral, transmucosal). Possible interactions with the active substance utilized which are known to those skilled in the art are also to be taken into account and, if possible, to be avoided.

The average particle size of the porous particles is preferably $\leq 2$ mm, more preferably $\leq 0.5$ mm, and even more preferably $\leq 200$ µm, especially $\leq 50$ µm.

The particle size may be set, for example, by grinding and/or sieving, but also by growing suitable crystals or by suitable precipitation methods known to those skilled in the art.

The particles used according to the invention are generally finely pored, the average pore or capillary diameter preferably being $\leq 0.1$ mm, more preferably $\leq 20$ µm, and particularly preferably $\leq 1$ µm.

The portion of active substance-containing particles, relative to the carrier matrix, can be varied within a wide range. To achieve a high load of active substance, the active substance-loaded particles may be contained in an administration form at a portion of up to 95%-wt, depending on the carrier matrix selected in a particular case. Therefore, the particle portion preferably amounts to 0.1 to 95%-wt., more preferably 5 to 60%-wt, with particular preference 5 to 25%-wt, each relative to the entire form of administration. Due to the wide range with regard to the particle content as well as with regard to the active substance amount, respectively the active substance concentration, in the individual particles, the inventive forms of administration are able to cover a broad range with regard to dosage.

However, it is to be taken into consideration that an excessively high portion of active substance-loaded particles may have an adverse effect on the physical properties of the carrier matrix. The upper limit for this portion can in each individual case be readily determined by experiments.

The loading of these porous or capillary-containing particles with active substance(s) may preferably be performed such that the liquid active substance, an active substance solution, dispersion, suspension or emulsion, or a liquid active substance preparation is mixed with a suitable quantity of particles, whereby the pores or capillary spaces are filled with active substance liquid or solution. Subsequently, the loaded particles can be separated from the excess active substance fluid or solution by methods known to those skilled in the art. Optionally, this may be followed by a drying process to remove any remaining residues of liquid or solvent.

According to a preferred embodiment, an active substance-containing solution is used which contains at least one solid active substance in dissolved form in a suitable solvent. This may also be a saturated active substance solution.

To facilitate entry of the active substance fluid into the interior of the particles upon loading of the particles, it may be necessary to add small amounts of surfactants or emulsifiers.

Apart from the porous particles already mentioned, those active substance-containing particles as can be obtained by the method described in WO 99/17868 and are designated as "concentrated powder form" (CPF) particles are also particularly preferred for making the inventive forms of administration. These are pulverulent, liquid-loaded particles or agglomerates of particles which are formed when an inert gas or gas mixture in a liquid active substance, an active substance-containing solution or suspension or any other liquid active substance preparation is dissolved in said liquid under pressure (preferably ca. 5 to 500 bar, especially preferably in the range from 10 to 250 bar) and the pressure on this solution is subsequently rapidly relieved (by means of a nozzle, for example) while simultaneously adding a pulverulent solid carrier material (carrier particles). The powders obtained in this manner are substantially dry and free-flowing and can contain up to 80%-wt of an active substance liquid. They have the advantage of being able to be processed like solid particles, despite their high liquid content.

The liquid contained is either present in the capillary spaces of the aggregated carrier particles, and/or in the pores of the carrier particles if open-pore carrier particles are used.

As pulverulent carrier substances, respectively carrier particles, one may, for instance, use starch types (such as maize, potato, wheat starch), silicic acid, respectively silicon dioxide, celluloses (e.g. microcrystalline celluloses, cellulose derivatives such as carboxymethyl cellulose, cellulose fibres); moreover it is also possible to use as particles porous particles of the kind mentioned at the outset, such as activated charcoal, zeolite, silicic acid, or polymers capable of swelling (especially so-called superabsorber polymers). "Polymers capable of swelling" is understood to preferably mean water-swellable polymers, e.g. polyvinyl alcohols with a high degree of hydrolysis, or high-molecular hydroxypropyl methyl cellulose.

The pulverulent carrier particles preferably have a particle size of less than 100 µm.

Further auxiliary substances considered for the manufacture of the pulverulent, liquid-filled particles are: common salt, sugar, dextrin, proteins, titanium dioxide, fats, polyglycols, magnesium stearate, highly dispersed silicon dioxide, glutamate, calcium, kaolin, polylactic acid, fats, waxes, thickeners.

To facilitate a subsequent resuspension of the liquid-filled particles it is also possible to add emulsifiers, such as phospholipids, especially lecithin, or partial glycerides during manufacture.

Inert gases considered are first of all carbon dioxide, gaseous hydrocarbons (e.g. methane, ethane, propane, butane), ether, nitrogen, dinitrogen monoxide, ammonia or inert gases.

The particles loaded according to the described process, too, will, if required, be separated from the excess active substance fluid, for instance by sedimentation or filtration.

Further processing and use of these particles, especially the manufacture of the inventive administration forms, may be performed in a fashion corresponding to that described above with respect to the first-mentioned form of the particles.

The following remarks apply to all of the various types of particles described:

According to a preferred embodiment, it is further provided for the particles, or at least a portion thereof, to be provided with a coating of fat- and/or water-soluble substances after loading with active substance. In this way it is, for instance, possible to achieve a control of the active substance release, in particular a control of the active substance release rate, or to improve the water-wettability. Materials considered for such coatings are, inter alia: film formers (e.g. polyacrylates, polymethacrylates), polyethylene glycols, vegetable or animal oils, liquid paraffin, polyvinyl pyrrolidone, cellulose derivatives.

To accelerate the active substance release upon application, it can be advantageous to select a water-soluble or biodegradable material as the material for the above-mentioned particles. In this case, exposure to body fluids (e.g. sweat, saliva, mucus) or enzymes, enables the degradation of the structure of the active substance particles, whereby the active substance contained is released more rapidly.

The present invention relates in particular to administration forms for application on the skin which are formulated as transdermal therapeutic systems (TTS). Generally, these administration forms are of a flat-shaped structure and enable the administration of systemically active medicinal active agents via the skin, it being possible to release said active agents to the skin, continuously over a predetermined period of time and at a defined release rate.

The TTS according to the invention comprise an active substance impermeable backing layer and a carrier matrix connected thereto, a plurality of particles having open pores or containing capillary spaces being embedded in the carrier matrix which serve as active substance reservoir and which contain at least one active substance in liquid form, as described above.

As base materials for making the carrier matrix in which the particles will be embedded, it is generally possible to use all those polymer materials which according to the state of the art are used for making active substance reservoir layers of TTS. In particular, the following substances may be used for producing the carrier matrix: polyacrylates, poly(meth)acrylates, copolymers of acryl and methacryl derivatives, and vinyl compounds (e.g. using the following monomers: acrylic acid, methacrylic acid, acrylic acid ethyl ester, acrylic acid butyl ester, acrylic acid octyl ester, 2-ethylhexyl acrylate, 2-hydroxyethyl acrylate and vinyl acetate); furthermore, polysiloxanes, preferably self-adhesive polysiloxanes, silicone rubbers; hydrocarbon polymers, preferably polyisobutylene, polyisoprene, styrene-isoprene-styrene block copolymers and styrene butadiene-styrene block copolymers; pressure sensitive adhesive preparations based on cellulose derivatives (e.g. ethyl cellulose, hydroxypropyl cellulose, hydroxypropyl methyl cellulose) and adhesive resins (e.g. colophony and colophony derivatives). Using the afore-mentioned materials it is possible to produce carrier matrices which have pressure-sensitive adhesive properties; such formulations, which are pressure-sensitive adhesive to the skin, are known to those skilled in the art. The pressure-sensitive adhesive surface of the TTS, by means of which the TTS is attached to the skin, is, in the state prior to application, covered with a detachable protective film.

Auxiliary substances which can be admixed to the carrier matrix may be, for example, plasticizers, fillers and skin penetration-enhancing substances (penetration enhancers). Substances suitable for this purpose are known to those skilled in the art.

To produce the TTS according to the invention, the carrier matrix materials may be processed both in dissolved form and as a melt if hot melt adhesives are used. In both cases, the porous particles filled with active substance liquid are incorporated homogeneously into the still-liquid or semi-solid carrier matrix preparation. If necessary, wetting agents (surfactants, e.g. SDS), emulsifiers (e.g. lecithin) etc. may be admixed to improve dispersion of the particles in the carrier matrix material.

Suitable as materials for the backing layer is a plurality of skin-tolerated plastics films such as, for instance, films made of polyvinyl chloride, ethylene vinyl acetate, vinyl acetate, polyethylene, polypropylene, or cellulose derivatives. Especially suitable materials for the backing layer are polyester films (e.g. polyethylene terephthalate). The afore-mentioned films are also suitable as materials for the detachable protective film, provided that they are rendered detachable by appropriate surface treatment such as siliconization.

In a further embodiment, the carrier matrix has a bi-layer or mono-layer structure, with at least one layer having embedded therein a plurality of particles with open pores or containing capillary spaces, which particles serve as active substance reservoir and contain at least one active substance in liquid form.

The liquid-filled, porous particles proposed by the invention can, in a corresponding fashion, also be used for preparing TTS which have a bag-shaped active substance reservoir filled with a liquid, high-viscous, semi-solid or thixotropic active substance-containing matrix, for example a gel. In this case, the liquid-filled particles are embedded in the matrix of the bag-shaped active substance reservoir.

Further especially preferred embodiments of the invention relate to mucoadhesive administration forms, e.g. mucoadhesive plasters or systems. For administration of active substances, these may be applied to the surfaces of mucous membranes (e.g. oral, nasal, vaginal mucous membrane), whereon they remain adhering. They have a solid or semisolid mucoadhesive carrier matrix wherein the active agent-containing particles are embedded or dispersed. They are substantially flat, and, like TTS, they may be provided on the back (opposite the mucoadhesive side) with a backing layer made of a plastics film.

For the production of the mucoadhesive carrier matrix, the following materials are considered with preference: Cellulose derivatives such as carboxymethyl cellulose sodium, carboxymethyl cellulose, hydroxypropyl cellulose, methyl cellulose, ethyl or propyl cellulose; polyvinyl alcohol, polyacrylic acid, polyacrylates, polyvinyl pyrrolidones, polyethylene oxide polymers; water-soluble polysaccharides of vegetable or microbial origin, especially pullulan, xanthan, alginates, starch, dextranes and pectins; gelatine and other gel-forming proteins. Suitable mucoadhesive formulations which start from the afore-mentioned substances are known to those skilled in the art.

Further preferred embodiments are active substance plasters for topical or epicutaneous administration of active substances to the skin. These may have a structure similar to that of the TTS described, with a solid or semi-solid carrier matrix which has embedded therein a plurality of particles having open pores or containing capillary spaces, which particles serve as active substance reservoir and contain at least one active substance, preferably in liquid form.

In all of the cases described above, the carrier matrix, wherein the active substance-containing particles are embedded, may optionally contain auxiliary substances apart from the matrix-forming base materials. Considered for this purpose are filling agents (e.g. $SiO_2$); thickening agents (e.g. alginates, pectin); colourants (e.g. quinoline yellow or $TiO_2$); emulsifiers (e.g. polyethoxylated sorbitan fatty acid esters such as TWEEN® or polyethoxylated fatty alcohols such as BRIJ®; skin-penetration enhancers (see above); plasticizers (e.g. polyethylene glycol, glycerol); sweeteners (e.g. aspartame, saccharine); preservative agents (e.g. sorbic acid and its salts), and flavouring agents.

"Active substances/agents" are understood to mean any medicinal agents used in the field of human or veterinary medicine, including vitamins, enzymes and hormones, as well as active substances for cosmetic treatments, and flavouring agents or aromatics. More particularly, the invention relates to medicinal active substances which can be absorbed via the skin or mucosa.

Especially preferred are active agents which are present in liquid state; the invention is furthermore applicable to a plurality of further active substances which can be brought into a liquid form, for instance as a solution, dispersion, suspension or emulsion.

The delivery of active substance(s) contained in the inventive forms of medicaments can be achieved in different ways. In the case of transdermal administration, or application to a mucosal surface, the active substance is able to diffuse out of the particles and be subsequently absorbed. If the administration form is constituted so as to be disintegratable or degradable, the particles can initially be released as such and subsequently the active agent contained in the particles can be released. If the particles are made of biodegradable material, the release may be influenced or accelerated by degradation of the particle material. In this way the present invention opens numerous possibilities of controlling the delivery of active substance.

Furthermore, the release of active substance can also take place in such a manner that the particles migrate or diffuse from the carrier matrix of the transdermal or transmucosal administration form through the skin or mucosa, and subsequently deliver the active substance to the circulation.

The invention further comprises processes for the manufacture of forms of medicaments for transdermal, transmucosal or epicutaneous administration, said manufacture starting from liquid active agents, active agent solutions or active agent preparations.

The inventive forms of administration may preferably be obtained by initially providing a carrier matrix material—as described above—which is suitable for the desired form of medicament, preferably in liquid or semi-solid form (e.g. as a solution or melt), or as a gel.

Then, a liquid active substance, an active substance solution or a liquid active substance preparation is provided. If the active substance itself is not present in liquid form, it is dissolved, dispersed or suspended in a pharmaceutically acceptable solvent or solvent mixture suitable for the active agent. The liquid active agent preparations may furthermore also contain active substance combinations. In a next process step, the liquid active substance, respectively the active substance solution, is mixed with particles having open pores or having capillary spaces (as described above), whereby the pores or capillary spaces will be filled with active substance liquid or active substance solution. This process can be assisted by addition of surfactants or emulsifiers.

After separating the particles from the excess active substance liquid or solution, optionally followed by a drying step, the particles, loaded with active substance liquid, are introduced into the carrier material mentioned in the first step and are incorporated therein and mixed therewith, so that the particles are homogeneously distributed in the carrier matrix. If necessary, wetting agents (surfactants, e.g. SDS), emulsifiers (e.g. lecithin) etc. can be admixed in order to improve the dispersion of the particles in the carrier matrix material.

Finally, depending on the type of medicament form to be made, it is possible to add and incorporate auxiliary agents (as mentioned above), and to carry through a further drying to achieve the desired consistency of the carrier matrix by solvent withdrawal.

The further processing of the medicament forms may be carried through by means of conventional methods, e.g. pressing, punching or coating.

The above-described process may be modified in various ways. The porous particles loaded with active substance may, for example, be provided with a coating prior to embedding in the carrier matrix, which coating prevents the diffusion of the active substance into the matrix (or into the solvent) as long as the matrix has not yet dried or solidified. Likewise, the particles may be provided with a fat-soluble and/or water-soluble coating prior to embedding, as mentioned hereinabove.

In a further, preferred manufacturing process of forms of medicaments for transdermal, transmucosal or epicutaneous administration, it is provided, as a modification of the above-described processes, that the production of the active substance-loaded particles is carried out in accordance with the process described in WO 99/17868, as described above ("concentrated powder form" (CPF) particles). This active substance-containing powder is then embedded in the carrier material, which his present in liquid or semisolid form; further processing is carried out as described above. Furthermore, this process of manufacture, too, can be modified in different ways, for example by applying coatings or covers to the particles prior to the embedding step.

Thus, the present invention advantageously enables the production of transdermal, epicutaneous or mucoadhesive forms of medicaments, especially of flat medicament forms, which can have a high content of an active substance present in liquid form.

The invention claimed is:

1. Forms of administration for application on the skin or mucosa, comprising a carrier matrix with pressure sensitive adhesive or mucoadhesive properties and at least one active substance, said carrier matrix having a plurality of porous particles which serve as active substance reservoir and contain at least one active substance, wherein said particles
are selected from the group consisting of open-cell particles of natural sponges, open-cell particles of synthetic sponges, and open-cell particles of solidified foams, the material for said synthetic sponges and solidified foams being selected from the group of solidified gelatine foam, collagen foams, polyurethane foams, microcellular polyester foams and polyether foams; or
are pulverulent, liquid-loaded particles or particle agglomerates which have been manufactured by dissolving an inert gas, under pressure, in an active substance-containing solution or suspension and subsequently releasing the pressure on the solution or suspension while simultaneously admixing a pulverulent, solid carrier material said carrier material being selected from the group consisting of starches and celluloses.

2. Forms of administration according to claim 1, characterized in that the average particle size of the particles is ≦2 mm.

3. Forms of administration according to claim 1 or 2 characterized in that the particles having pores or capillary spaces are finely pored, with an average pore or capillary diameter of ≦0.1 mm.

4. Forms of administration according to claim 1, characterized in that the portion of the particles, relative to the carrier matrix, amounts to 0.1 to 95%-wt.

5. Form of administration according claim 1, characterized in that the particles contain swellable, liquid-absorbing polymers as carrier material.

6. Form of administration according claim 1, characterized in that the particles contain the active substance(s) in liquid form or contain an active substance-containing solution which contains at least one solid active substance in dissolved form in a suitable solvent.

7. Forms of administration according claim 1, characterized in that at least a part of the active substance-loaded particles is provided with a coating which inhibits or slows down the diffusion of the active substance to its environment at least temporarily.

8. Forms of administration according to claim 1, characterized in that they contain particles loaded with different active substances.

9. Forms of administration according to claim 1 characterized in that different particle types and particle sizes are used.

10. Forms of administration according to claim 1, characterized in that they contain particles loaded with liquid plasticizers and/or skin-penetration enhancers.

11. Forms of administration according to claim 1, characterized in that they contain particles which are water-soluble or biodegradable.

12. Forms of administration according to claim 1, characterized in that they are formulated as transdermal therapeutic systems (TTS) which have an active substance-impermeable backing layer and a carrier matrix connected thereto, with a plurality of particles being embedded in the carrier matrix which have open pores or contain capillary spaces and which serve as active substance reservoir and contain at least one active substance.

13. Transdermal therapeutic systems according to claim 12 characterized in that the carrier matrix has pressure-sensitive adhesive properties and, in the state prior to application, is covered with a detachable protective film.

14. Transdermal therapeutic systems according to claim 12 or 13, characterized in that the carrier matrix is a bi-layer or mono-layer matrix, with a plurality of particles being embedded in at least one layer thereof which have open pores or contain capillary spaces and which serve as active substance reservoir and contain at least one active substance.

15. Forms of administration according to claim 1, characterized in that they are formulated as transmucosal forms of administration and have a solid or semi-solid carrier matrix, in which matrix there is embedded a plurality of particles which have open pores or contain capillary spaces and which serve as active substance reservoir and contain at least one active substance.

16. Forms of administration according to claim 1, characterized in that they are formulated as active substance plasters for topical or epicutaneous administration of active substances and comprise a solid or semi-solid carrier matrix, in which matrix there is embedded a plurality of particles which have open pores or contain capillary spaces and which serve as active substance reservoir and contain at least one active substance.

17. Forms of administration according to claim 1, wherein the average particle size of the particles is 0.5 mm.

18. Forms of administration according to claim 1, wherein the average particle size of the particles is 200 μm.

19. Forms of administration according to claim 1 or 2, wherein the particles having pores or capillary spaces are finely pored, with an average pore or capillary diameter of 20 μm.

20. Forms of administration according to claim 1 or 2, wherein the particles having pores or capillary spaces are finely pored, with an average pore or capillary diameter of 1 μm.

21. Forms of administration according to claim 1, wherein the portion of the particles, relative to the carrier matrix, amounts to 5-60%-wt.

22. A form of administration according to claim 5, wherein the swellable, liquid-absorbing polymers are superabsorbing polymers.

23. A form of administration according to claim 5, wherein the swellable, liquid-absorbing polymers are water swellable polymers.

24. A form of administration according to claim 5, wherein the swellable, liquid-absorbing polymers are selected from the group consisting of polyvinyl alcohol having a high degree of hydrolysis and high-molecular hydroxypropylmethyl cellulose.

25. A form of administration according to claim 6, wherein the active substance-containing solution is a saturated active substance solution.

26. Forms of administration according to claim 12, 15, or 16, wherein the active substance is present in a liquid form.

27. A transdermal therapeutic system according to claim 14, wherein the active substance is present in a liquid form.

28. Forms of administration according to claim 12, wherein said carrier matrix comprises polyacrylates or poly(meth)acrylates.

29. Forms of administration according to claim 12, wherein said carrier matrix comprises polysiloxanes.

30. Forms of administration according to claim 12, wherein said carrier matrix comprises polyisobutylene, polyisoprene, styrene-isoprene-styrene block copolymers or styrene-butadiene-styrene block copolymers.

31. Forms of administration according to claim 12, wherein said carrier matrix comprises pressure-sensitive adhesive preparations based on cellulose derivatives and adhesive resins.

32. Forms of administration according to claim 15, wherein said carrier matrix is a mucoadhesive carrier matrix produced from cellulose derivatives.

33. Forms of administration according to claim 32, wherein said cellulose derivatives comprise carboxymethyl cellulose sodium, carboxymethyl cellulose, hydroxypropyl cellulose, methyl cellulose, ethyl cellulose and propyl cellulose.

34. Forms of administration according to claim 15, wherein said carrier matrix is a mucoadhesive carrier matrix produced from polyvinyl alcohol, polyacrylic acid, polyacrylates, polyvinyl pyrrolidones or polyethylene oxide polymers.

35. Forms of administration according to claim 15, wherein said carrier matrix is a mucoadhesive carrier matrix produced from water-soluble polysaccharides of vegetable or microbial origin.

36. Forms of administration according to claim 15, wherein said carrier matrix is a mucoadhesive carrier matrix produced from gel-foaming proteins.

37. Forms of administration for application on the skin or mucosa, comprising a carrier matrix with pressure-sensitive adhesive or mucoadhesive properties and at least one active substance, said carrier matrix having embedded therein a plurality of porous particles which serve as active substance reservoir and contain at least one active substance, wherein said particles are open-cell particles of natural sponges, or open-cell particles of synthetic sponges, or open-cell particles of solidified foams,
the material for said synthetic sponges and solidified foams being selected from the group of solidified collagen foams, polyurethane foams, microcellular polyester foams and polyether foams.

38. Forms of administration for application on the skin or mucosa, comprising a carrier matrix with pressure-sensitive adhesive or mucoadhesive properties and at least one active substance, said carrier matrix having embedded therein a plurality of porous particles which serve as active substance reservoir and contain at least one active substance, wherein said particles are pulverulent, liquid-loaded particles or particle agglomerates which have been manufactured by dissolving an inert gas, under pressure, in an active substance containing solution or suspension and subsequently releasing the pressure on the solution or suspension while simultaneously admixing a pulverulent, solid carrier material, wherein starches or celluloses are used as said carrier material.

39. Forms of administration for application on the skin or mucosa, comprising a carrier matrix with pressure-sensitive adhesive or mucoadhesive properties and at least one active substance, said carrier matrix having a plurality of porous particles which serve as active substance reservoir and contain at least one active substance, wherein said particles
are open cell particles of natural sponges, or open-cell particles of synthetic sponges, or open cell particles of solidified foams,
the material for said synthetic sponges and solidified foams being selected from the group of solidified gelatine foam, collagen foams, polyurethane foams, microcellular polyester foams and polyether foams,
and wherein said particles contain said at least one active substance in liquid form or contain an active substance-containing solution which contains said at least one active substance in dissolved form in a suitable solvent.

* * * * *